United States Patent [19]
Belcour-Castro et al.

[11] Patent Number: 5,989,876
[45] Date of Patent: Nov. 23, 1999

[54] COLORANT PRECURSORS DERIVABLE FROM CELLS OF PLANTS OF THE GENUS MEDICAGO, PROCESS FOR THEIR PREPARATION AND USE THEREOF FOR THE PREPARATION OF COLORANTS

[75] Inventors: Béatrice Belcour-Castro, La Riche; Georges Hussler, Aulnay-Sous-Bois; Anne Bonnet, Paris, all of France

[73] Assignee: L'Oreal, Paris, France

[21] Appl. No.: 08/988,425

[22] Filed: Dec. 10, 1997

[30] Foreign Application Priority Data

Dec. 11, 1996 [FR] France ................................. 96 15212

[51] Int. Cl.$^6$ .............................. C12N 5/00; A61K 7/06; A61K 7/13; C07D 209/12
[52] U.S. Cl. ........................... 435/117; 435/41; 435/121; 435/122; 435/410; 424/195.1; 424/70.1; 424/70.6; 424/74; 514/183
[58] Field of Search ............................. 435/41, 117, 410, 435/121, 122; 424/195.1, 70.1, 70.6, 74; 514/183

[56] References Cited

U.S. PATENT DOCUMENTS 4,569,839  2/1986  Grollier et al. ........................... 424/74

FOREIGN PATENT DOCUMENTS 0 560 683  9/1993  European Pat. Off. .
WO 82 01010  4/1982  WIPO .

OTHER PUBLICATIONS

Database WPI Section Ch, Week 9411 Derwent Publications Ltd., London, GB; Class B04, AN 94–089261 XP002038421 & JP 06 040 884 A (Taiyo Kagaku KK), Feb. 15, 1994.

Chemical Abstracts, vol. 97, No. 13, Sep. 27, 1982 Columbus, Ohio, US; abstract No. 107154, Chaubet, Nicole et al: Characterization of.beta.–galactosidase of Medicago sativa suspension–cultured cells growing on lactose. Effect of the growth substrates on the activities: XP002038420 & Z. Pflanzenphysiol. (1982), 106(5), 401–7.

*Primary Examiner*—Leon B. Lankford, Jr.
*Attorney, Agent, or Firm*—Nixon & Vanderhye, P.C.

[57] ABSTRACT

Colorant precursors, which are present in the cells of plants belonging to the genus Medicago, such as alfalfa, can react with quinones so as to yield colorants which can be used in dyeing compositions for textiles or hair.

33 Claims, No Drawings

COLORANT PRECURSORS DERIVABLE FROM CELLS OF PLANTS OF THE GENUS MEDICAGO, PROCESS FOR THEIR PREPARATION AND USE THEREOF FOR THE PREPARATION OF COLORANTS

The present invention claims benefit to Application No. 96 15212 filed in France on Dec. 11, 1996, the entire contents of which are incorporated herein by reference.

The invention concerns a colorant precursor derivable from cells of plants belonging to the genus Medicago, as well as the process for preparation of said colorant precursor and the use thereof for the preparation of colorants by means of reaction with a quinone.

Conventional practice encompasses numerous quinone-derived colorants and the use thereof, in particular in the dyeing of keratinous fibers (see, for example, patent application Ser. No. EP-A-0560683 and the documents cited in this application.

It has now been discovered that cells of plants of the genus Medicago, when grown in vitro in the presence of lactose used as a carbon-containing substrate, contain metabolites which can react with quinones so as to yield colorants, and that these metabolites are lacking when glucose is employed as the carbon-containing substrate.

It is these metabolites which constitute the colorant precursors according to the invention. It has been found that these colorant precursors are also found in plants belonging to the genus Medicago grown in the soil or hydroponically, but in a very low concentration.

Accordingly, the invention concerns a composition containing at least one colorant precursor characterized by the fact that said colorant precursor exists naturally in the cells of plants of the genus Medicago, can react in aqueous solution with 1,4-naphthoquinone so as to yield at least one colorant, and is present in said composition in an at least partially purified state.

The expression "in an at least partially purified state" here means that, in comparison with its natural state (fresh or dried plant or cells), the colorant precursor in the invention composition has been concentrated and/or that at least some of the other plant constituents have been removed, in particular constituents having a molar mass higher than 3,500.

In compositions according to the invention, the colorant precursor is normally present in a concentration greater than the concentration of said precursor in said dried plant or dried cells.

A plant is judged to be dried when the water content thereof is less than 10% by weight.

The invention relates, in particular, to a composition in which said precursor exists in a concentration at least equal to the concentration of said precursor in an aqueous dispersion which contains, per liter of dispersion, 1 gram (and, in particular, 2 grams) of the ground product of cells from said plant used as dry matter, the cells of said ground product having been grown in vitro in a medium containing only lactose as the carbon source.

The colorant precursors which are constituents of the composition according to the invention are found in the plants and cells cultivated in vitro (for example under the conditions specified below) and belonging to the following species: *Medicago sativa, Medicago falcata, Medicago intermedia, Medicago media, Medicago varia*, and *Medicago versicolor*.

The in vitro cultivation of said plants may be carried out starting with an explant (for example a leaf or cotyledon fragment).

Cultivation mediums suitable for in vitro cultivation of plant cells are currently well known. These cultivation mediums most notably contain nitrogen and carbon sources, microelements, and vitamins in low concentrations. Current cultivation mediums are prepared in accordance with the theoretical foundations laid down by Murashige and Skoog when the cultivation medium bearing their names was being perfected. The microelements normally used are those suggested by Heller: manganese, zinc, boron, copper, iodine, nickel, aluminum, molybdenum, iron, and cobalt. Carbon sources normally include sugars, in particular saccharose and glucose; however, to produce the colorant precursors according to the invention, these sugars should be replaced at least partially by other carbon sources, most notably lactose. Suitable carbon sources can be selected by simply routine experiments, while searching for the presence, in cultivated cells, of a colorant precursor such as that specified in the present application. Among the vitamins which promote the growth of cultured cells, mention is made of thiamine, and also nicotinic acid and pyridoxine. These vitamins also include calcium panthothenate, biotin, and meso-inositol.

The growth medium may also contain amino acids, protein extracts, organic acids, etc. Growth regulating agents, such as napthaleneacetic acid (ANA), kinetin (6-furfurylaminopurine), etc., The compositions of the colorant precursor according to the invention are, in particular solutions (that is, solutions virtually totally free of undissolved solid products) or solids which can be obtained, for example, by starting with such solutions and by evaporation of the solvent or solvents. The solid residues produced by evaporation of the solvent (most notably water, lower alkanol, and mixtures thereof) are virtually totally soluble in such a solvent.

The invention also relates to a process for preparation of a composition such as that previously specified.

This process is basically characterized by the fact that plants or plant parts belonging to the genus Medicago, or cells from a plant of the genus Medicago taken from in vitro cultivation, are ground, and that using conventional fractionation techniques, a fraction of the ground product obtained is separated out and collected, said fraction being at least partially purified and free of constituents having a molar mass higher than 3,500. To separate out said at least partially purified fraction, the procedure may be carried out using at least one of the following techniques:

filtration is effected and the filtrate collected, decantation or centrifugation is carried out, and a fraction containing the supernatant is collected, or extraction is performed using a solvent.

Simple routine experiments permit selection of a suitable solvent for extraction. Use may be made of water or a lower alkanol (for example methanol or ethanol). Next, the solvent may be evaporated to obtain a composition existing as a dry extract. A ground product, extract, filtrate, or supernatant obtained in this way is treated so as to eliminate the constituents having a molar mass of more than 3,500, and, in particular, greater than 1,500.

According to a special embodiment of the process for preparation of the colorant precursor composition, cells from a plant of the genus Medicago are grown in vitro in a medium containing a suitable carbon source, and, as before, a fraction of said ground product containing the at least partially purified colorant precursor is separated out and collected.

Cultivation may take possible in a medium containing only lactose as the carbon source.

In vitro cultivation may be carried out in light, but is preferably conducted in the dark. The medium is either not stirred, or, preferably, stirred. The cultivation temperature may vary between 20 and 30° C. The biomass is collected following a sufficient cultivation time, which is a function, in particular, of the volume of fermentor. In addition, in the event of continuous cultivation, samples of a portion of the biomass may be drawn at regular intervals. In each case, the cultivation time or the intervals between two samplings may be determined by routine experiments.

In order to use the compositions according to the invention, the process for preparation of these compositions thus includes a step involving grinding of the biomass (plants, parts of plants, or cells cultivated in vitro) using conventional methods. It is then possible to purify the composition at least partially, by removing all or a portion of the constituents other than the colorant precursors, as previously indicated. For example, the ground product may be filtered on any suitable filter, including one which captures products measuring more than approximately 0.2 µm.

The composition according to the invention (filtrate, supernatant, or extract) can be purified still further by passing it through an ultrafiltration or dialysis membrane capable of capturing constituents having a molar mass greater than a predetermined threshold, for example greater than 3,500, or greater than 1,500 or 1,000. In each case, the colorant precursors are contained in the filtrate or dialysate.

The colorant precursors according to the invention are captured by membranes possessing a cutoff threshold of 500 daltons. The molar mass thereof thus ranges between 500 and 1,000 daltons.

The invention further relates to a process for producing a colorant, which is characterized by the fact that a quinone is reacted with a colorant precursor composition such as that specified above, and that, if desired, a coloring product produced by this reaction is isolated and/or purified.

The selection of suitable quinones may be made based on simple routine experiments by reacting the quinone under consideration with a composition containing the colorant precursor specified above. Indeed, the reaction leads to the emergence of coloration or color modification; the quinone being considered can be used in the process for preparation of a colorant according to the invention.

According to a special embodiment, the quinone can be selected among 1,4-benzoquinones potentially substituted in at least either of positions 2 and 3, 1,4-naphthoquinones potentially substituted in at least one of positions 5, 6, 7 and 8, and diphenoquinone.

Among the potentially-substituted 1,4-benzoquinones, mention will be made in particular of those corresponding to formula (I):

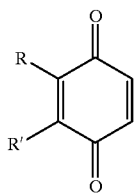

(I)

in which R and R' represent, separately, —H, hydroxy, $C_1$–$C_4$ alkyl, $C_1$–$C_4$ alkoxy, sulfonyl, or a optionally-substituted heterocyclic or aryl group. The heterocyclic group is, for example, a optionally-substituted furanyl, pyranyl, or indolyl group, in particular substituted by an alkyl or alkoxy group of $C_1$–$C_4$. The aryl group is, for example, a potentially-substituted phenyl group, in particular substituted by at least one $C_1$–$C_4$ alkyl or $C_1$–$C_4$ alkoxy.

Potentially-substituted 1,4-naphthoquinones include those corresponding to formula (II):

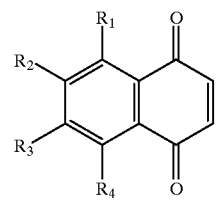

(II)

where the substituents $R_1$–$R_4$ are defined, separately, as are R and R', above.

The quinones corresponding to formulae (I) and (II) are conventionally known or may be prepared in accordance with conventional procedures. Some usable quinones, including compounds corresponding to formulae (I) and (II) are described, for example, in Patent No. EP-376776 and the *Dictionary of Natural Products on CD-ROM*, Chapman and Hall (London), 1996.

In particular, use may be made of a quinone chosen from 1,4-benzoquinone, 2-methyl-1,4-benzoquinone, 2-methyl-1,4-benzoquinone, 2-(4-methyl-2-furanyl)-1,4-benzoquinone, 2-hydroxy-1,4-benzoquinone, 2-phenyl-1,4-benzoquinone, 1,4-naphthoquinone, 5-hydroxy-1,4-naphthoquinone, 5-hydroxy-7-methyl-1,4-naphthoquinone, 6-methyl-1,4-naphthoquinone, and 5,8-dihydroxy-1,4-naphthoquinone.

Other quinone derivatives, such as geogenine (or pleurotine) and juglorine may also be used.

The reaction of the colorant precursor with a quinone is preferably carried out in solution in a suitable solvent, such as an alcohol or a water-alcohol mixture. The alcohol may be a lower alkanol, such as methanol. For example, the quinone may be added as a solution in alcohol to an aqueous solution containing the colorant precursor. The reaction may be carried out at a temperature of between approximately 20 and 100° C., and, in particular, from about 30 to 80° C.

The colorant precursors according to the invention may be present in the whole plants grown in soil or in hydroponic cultivation. Thus, when using *Medicago sativa*, the filtrate obtained after passing the ground product of a whole plant through a membrane possessing a porosity of 0.2 µm yields colorant precursors similar to those present in cells cultivated in vitro in the presence of lactose, as shown, for example, by HPLC analysis of a filtrate of this kind. However, in the whole plants, these colorant precursors are most often present only in low concentrations, which are normally several hundreds of times lowers than the concentrations obtained in the cells of the same plant cultivated in vitro in the presence of lactose as the sole carbon source. The compositions according to the invention as specified above are those containing the colorant precursors in a concentration that is at least equal to the concentration of said precursors in an aqueous dispersion containing, per liter of dispersion, 1 g (and, in particular, 2 g) of a ground product composed of cells of the plant in question as the dry matter, the cells of said ground product having been cultivated in a medium containing only lactose as the carbon source. The minimum concentrations thus specified, which may be quite easily achieved by using as raw material cells cultivated in vitro in the presence of a carbon source such as lactose, are appreciably greater than the concentrations that may be achieved in an aqueous dispersion of a ground product of the whole plant.

The invention also concerns a colorant characterized by the fact that it can be obtained by implementing the process just described.

These colorants including compounds A, B, C, and D, which are described below in the experimental section.

Among the colorant precursors contained in the compositions according to the invention, mention may be made of those which can react with 1,4 naphthoquinone so as to yield at least one of said compounds A, B, C, and D.

The colorants produced according to the invention are normally soluble in at least one normally-used solvent, for example in alcohols (in particular lower alkanols such as methanol or ethanol) and in mixtures of water and an alcohol.

These colorants may be used in dyeing compositions, such as compositions for dyeing woven fibers, including wool; in hair-dyeing compositions; in nail polishes, etc. Such compositions falls within the scope of the invention. They may also be used to impart distinctive coloration to liquid compositions, such as compositions used to clean or maintain surfaces such as floors, walls, and windows.

The dyeing compositions according to the invention may be prepared using conventional methods. For example, hair-dyeing compositions containing colorants produced according to the invention include at least one suitable, cosmetically-acceptable solvent, including water, lower alcohols (for example, $C_1$–$C_6$ alcohols), alkylene glycols (such as ethylene glycol and propylene glycol), etc.

The colorants obtained according to the invention are present in hair-dyes in a concentration normally ranging between 0.01 and 10% by weight, and specifically between 0.05 and 5% by weight, of the total weight of the composition. These compositions may also contain other colorants chosen from conventional direct colorants, as well as ingredients normally present in this type of composition, for example surfactants, thickening agents, dispersants, preservatives, agents used to swell keratinous fibers, perfumes, etc.

The dyeing compounds according to the invention may exist as lotions, gels, dispersions, emulsions, foams, or in aerosol form.

To dye hair with the dyeing compositions according to the invention, the composition is applied to the hair and allowed to work (when the composition is designed to be rinsed) for a period of between 5 and 60 minutes, and, in particular, between 10 and 30 minutes; next, the hair is rinsed. When the composition is not intended to be rinsed, it is applied to the hair, which can then be dried.

Nail polish compositions containing the colorants obtained in accordance with the invention are conventionally prepared. They normally contain, in addition to the colorant obtained according to the invention, in a solvent or suitable solvent mixture (in particular alcohols such as lower alkanols or benzyl alcohol, the acetates thereof, and acetone or glycols), a film-forming polymer (in particular nitrocellulose, ethyl cellulose, etc.), a plasticizing agent (for example butyl phthalate) which enhances the pliability of the nail polish film applied, potentially other colorants or pigments, and resins which give a high-gloss polish and possess good adhesion.

The dyeing compositions according to the invention may also be used in procedures involving dyeing of woven fibers, such as wool, by impregnation or immersion of the woven fibers or fabrics in a solution or dispersion of the colorant obtained according to the invention, potentially in the presence of a mordant, using conventional methods.

The invention also concerns a kit making it possible to prepare a dyeing composition. This kit includes, in separate containers whose contents are mixed at the time of use, at least one colorant precursor and at least one quinone, said precursor possessing the following characteristics:

it exists naturally in the cells of a plant belonging to the genus Medicago, it can react with said quinone while yielding at least one colorant.

In the kit according to the invention, the colorant precursor may exist in solution in a solvent such as those cited above with respect to reactions with quinone. The colorant precursor may also exist as a dried extract or purified product. In this latter case, the kit may contain at least one such solvent in a separate container, whose contents are used to dissolve the reagents (colorant precursor and/or quinone) at the time of use. Similarly, quinone may be present as a pure product or in solution form.

The following examples illustrate the invention.

EXAMPLE 1: IN VITRO CULTIVATION IN THE DARK IN THE PRESENCE OF LACTOSE

An alfalfa (European variety) cotyledon fragment was cultivated in a liquid medium under aseptic conditions. The cultivation medium, which had the particularity of containing lactose as the carbon-containing substrate, had the following composition:

| Constituents | Concentrations (mg × $L^{-1}$) |
| --- | --- |
| $KNO_3$ | 1,900.000 |
| $NH_4NO_3$ | 1,650.000 |
| $KH_2PO_4$, $H_2O$ | 170.000 |
| $MgSO_4$, $7H_2O$ | 370.000 |
| $CaCl_2$, $2H_2O$ | 440.000 |
| $MnSO_4$, $H_2O$ | 0.076 |
| $NiCl_2$, $6H_2O$ | 0.030 |
| $AlCl_3$, $6H_2O$ | 0.050 |
| $H_3BO_3$ | 1.000 |
| $ZnSO_4$, $7H_2O$ | 1.000 |
| $CuSO_4$, $5H_2O$ | 0.030 |
| KI | 0.010 |
| $FeSO_4$, $7H_2O$ | 27.800 |
| $Na_2ETDA$ | 37.300 |
| Calcium panthothenate | 1.000 |
| Meso-inositol | 100.000 |
| Nicotinic acid | 1.000 |
| Pyridoxine | 1.000 |
| Thiamine | 1.000 |
| Biotin | 0.010 |
| Kinetin | 0.100 |
| Naphthaleneacetic acid | 0.100 |
| Lactose | 30,000.0 |

This cultivation medium was preliminarily sterilized in an autoclave for 20 minutes at 115° C.

To maintain the culture, cells were collected by filtration on a 50 μm Blutex cloth and pure culture medium contained in 1 L Erlenmeyer flasks containing 400 mL medium was inoculated, with 20 g of the biomass collected. The culture was kept at 26° C. in the dark while stirring at 100 rpm. The culture was maintained on a weekly basis.

EXAMPLE 2: EXTRACTION AND CHARACTERIZATION OF THE COLORANT PRECURSOR: REACTION WITH 1,4-NAPHTHOQUINONE a) Preparation of the Colorant Precursor in Filtered Solution Form Cells cultivated as in Example 1 were collected at the end of a maintenance cycle by filtration of 50 μm Blutex cloth. 5 g of the fresh material thus collected were added to 15 cm³ of a buffered solution, pH=6.5.

The buffer solution was prepared in the following manner: solution A containing 27.8 g $NaH_2PO_4$, $2H_2O$ in 1 L ultrapure water was prepared. Solution B containing 53.65 g $Na_2HPO_4$, $7H_2O$ in 1 L ultrapure water was prepared. 171.25 mL of solution A were mixed with 78.75 mL of solution B and 250 mL ultrapure water in order to obtain 500 mL of the buffered solution.

The cell suspension was ground in a Potter blender. The ground mixture was filtered on a 2.7 μm Whatmann filter, then the filtrate obtained was filtered on a 0.2 μm Millipore membrane. Filtration was carried out at 4° C.

b) Reaction with 1,4-naphthoquinone

50 μL of a solution containing 12.5 g/L of 1,4-naphthoquinone in methanol were added to 5 $cm^3$ of the filtrate produced. The mixture obtained was left to incubate for 90 minutes at 30° C.

c) Extraction of the Coloring Product

Next, an aqueous solution of 1 N chlorhydric acid was added until reaching a pH of 2.5, and methylene chloride was added in a proportion of one volume per volume of reaction medium. The mixture was stirred for one hour using a magnetic bar and centrifuged for 10 minutes at 10,000 rpm. The organic and aqueous phases were separated out. Ethyl acetate was added to the aqueous phase (1 volume ethyl acetate per volume of aqueous phase). Stirring took place for one hour, then the mixture was allowed to decant and the organic and aqueous phases were separated out.

The organic phases were combined and dried on anhydrous sodium sulfate. The sodium sulfate was then removed by filtration. Next, the solvents were evaporated under reduced pressure at 50° C. A dry residue was produced.

d) Analysis of the Extract Produced

The dry residue obtained during the preceding stage, which was dissolved in a 50:50 (by volume) methanol/methylene chloride mixture, was analyzed by silica thin layer chromatography. Elution took place using methylene chloride containing 1% methanol.

The presence of a product A, characterized by Rf=0.88, and of a product B, characterized by Rf=0.85, was observed.

The extract was also analyzed in HPLC, using a Lichrosorb (R) RP HPLC column made by Merck. The eluent was a 60/40 (v/v) mixture of acetonitrile and ultrapure water acidified to a pH of 3 using phosphoric acid. Flow rate: 1 $cm^3$ per minute.

Detection was carried out at 490 nm. Products A and B were characterized by retention times of 22.7 and 13.8 minutes, respectively.

Thin layer chromatography analysis of the dry residue obtained during the preceding stage, using as eluent a 98:2 mixture of methylene chloride and methanol, in solution in a 50:50 mixture of methylene chloride and methanol also made it possible to separate out a compound C, which had a purple color (Rf=0.2).

Thin layer chromatography analysis of the dry residue obtained during the preceding stage, using as eluent a 85:15 mixture of methylene chloride and heptane, in solution in a 50:50 mixture of methylene chloride and methanol also made it possible to separate out a compound D, which had a yellow color (Rf=0.14).

Compounds A, B, C, and D were analyzed by mass spectrometry in RMN1H, TMN13C, RMN 2D1H-13C and 1H-15N.

The analytical data in their entirety allow us to suggest the following structures:

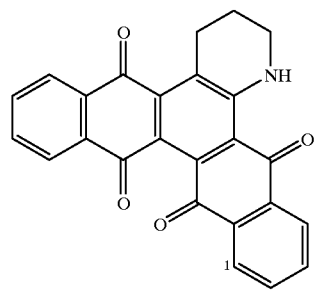

Compose A
Compound A

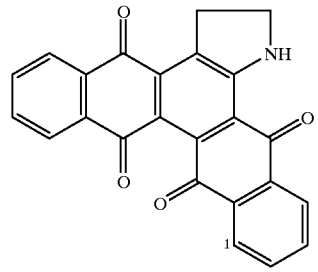

Compose B
Compound B

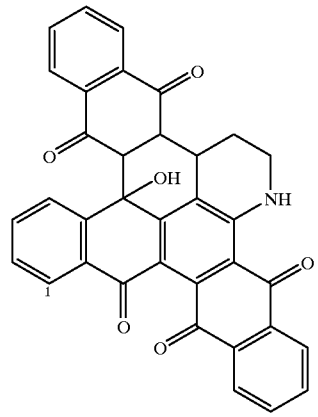

Compose C
Compound C

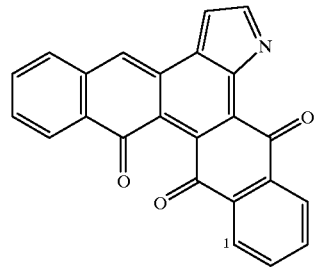

Compose D
Compound D

Accordingly, compound A was 6,7,8,9-tetrahydro-dinaphtho[2,3-f:2',3'-h]quinoline-5,10,11,16-tetraone; compound B was dinaphtho[2,3-c;2', 3'-g]indoline-5,9,14,15-tetraone; compound C was 4b-hydroxy-4b,4c, 10a,10b,11,12,13-heptahydro-3-aza-anthra[1,4-def]naphtho[2',3'-p]chrysene-5,10,14,19,20-pentaone, and compound D was dinaphtho[2,3-e;2',3'-g]indole-5,14,15-trione.

In solution in methylene chloride, compounds A, B, and C are red, and compound D, yellow.

In other experiments, the filtrate obtained in Example 2a) above was treated in an autoclave for 30 minutes at 120° C. After adding naphthoquinone and incubating as stated above, no formation of compounds A and B took place. On the other hand, treating the filtrate for 30 minutes at 80° C. did not prevent formation of products A and B.

When the filtrate produced as previously specified was preliminarily treated with a protease in a final concentration of 80 units for 15 hours at 40° C., products A and B formed in detectable quantities, after reaction with 1,4-naphthoquinone under the conditions previously specified.

In other experiments, the filtrate produced in Example 2a) above was dialyzed across different membranes having cutoff thresholds of 3,500, 1,000, and 500 daltons. In each case, reaction with 1,4-naphthoquinone followed by extraction as described above was carried out both on the dialysis residue and on the dialysate, and the products obtained were analyzed using thin layer chromatography, while looking for products A and B.

Using membranes having a cutoff threshold of 3,500 and 1,000 daltons, products A and B were detected in the product yielded by reaction with the dialysate. Using the membrane having a cutoff threshold of 500 daltons, products A and B were found in the product obtained from reaction with the dialysis residue.

It may thus be concluded that the colorant precursors present in the filtrate, which reacted with 1,4-naphthoquinone, had a molar mass of between 500 and 1,000 daltons, and that reaction with 1,4-naphthoquinone was not enzymatic in nature.

EXAMPLE 3: IN VITRO CULTIVATION UNDER ILLUMINATION: COMPARISON WITH CELLS CULTIVATED IN THE PRESENCE OF GLUCOSE

When alfalfa cells cultivated in the same medium as that used in Example 1 were cultivated under illumination (16 hour photoperiod), products A and B also formed after reaction with 1,4-naphthoquinone, as described in Example 2.

Various tests comparable to those in Example 2 were carried out on cultures of *Medicago saliva* cultivated on the same medium as that described above, but in the presence of glucose as carbon source, instead of lactose. Products A and B were not obtained in detectable quantities after reaction with 1,4-naphthoquinone.

EXAMPLE 4: REACTION WITH P-BENZOQUINONE

The procedure implemented was similar to that described in Example 2b), replacing 1,4-naphthoquinone with p-benzoquinone. The reaction mixture obtained had a purple color.

EXAMPLE 5: REACTION WITH JUGLONE

The procedure implemented was similar to that described in Example 2b), replacing 1,4-naphthoquinone with 5-hydroxy-1,4-naphthoquinone (juglone). A brown color was produced.

EXAMPLE 6: REACTION WITH NAPHTHAZARINE

The procedure implemented was similar to that described under Example 2b), replacing 1,4-naphthoquinone with 5,8-dihydroxy-1,4-naphthoquinone (naphthazarine). A pink color resulted.

EXAMPLE 7: ANALYSIS OF DYEING POWER

Tests were carried out on hair batches containing 90% naturally white hair.

Tests were also conducted on the same hair which had been preliminarily permed with DULCIA 1 (R) permanent made by L'Oréal.

The extract obtained in Example 2c) was dissolved in 95% ethanol.

Composition 1: An equal volume of water to which citric acid was added to reach a pH of 4 was added to the ethanol.

Composition 2: An equal volume of water to which monoethanolamine was added to reach a pH of 10.5 was added to the ethanol solution.

Tufts of hair weighing 1.2 g were immersed in composition 1 or 2 and left for 30 minutes at 45° C., then the tufts were rinsed and the hair dried.

In all cases, a tobacco brown color was obtained, which was more pronounced on the permed hair.

EXAMPLE 8: COMPOSITION OF THE HAIR DYE

| | |
|---|---|
| Compound A | 0.1 g |
| Vinyl acetate/crotonic acid/polyethylene glycol copolymer sold under the trade name "Aristoflex A" by the Hoechst company | 1.5 g |
| Ethanol | 40 g |
| Triethanolamine: quantity sufficient to raise the pH to 7 | 100 g |
| Water: quantity sufficient for | 100 g |

This lotion was applied to white hair. The hair was then shaped and dried. It had a red coloration.

Similar results were obtained by replacing compound A with compound B or C or by mixing compounds A, B, and C in equal quantities.

EXAMPLE 9: NAIL POLISH COMPOSITION A composition for coloring nails having the following composition (% by weight) was prepared:

| | |
|---|---|
| Toluene | 21.97 |
| Butyl acetate | 10 |
| Ethyl acetate | 10 |
| n-propyl acetate | 10 |
| Isopropanol | 25 |
| Nitrocellulose | 9 |
| Dibutyl phthalate | 2 |
| Santolite | 3 |
| Polyvinyl butyral | 5 |
| Acetyl-tributyl-citrate | 3 |
| UV screen | 0.5 |
| Colorant | 0.53 |

When the colorant was compound A, B, or C, a pink-red nail polish was obtained. Using compound D, the nail polish was yellow.

EXAMPLE 10: KIT 1 The coloration reaction was carried out using a kit composed of 2 reagents:

a reagent A consisting of a glass 10 mL flask containing 50 μL of a methanol solution of 1,4-naphthoquinone in a concentration of 12.5 g/L, a reagent B consisting of a glass 5 mL flask containing 5 mL reagent prepared as follows: alfalfa cells (5 g) were ground in a buffer, as described in Example 1. The medium obtained was filtered under aseptic conditions on a 0.2 μ Millipore membrane. 5 ML of this mixture were transferred aseptically to a glass flask preliminarily sterilized in an autoclave at 120° for 30 minutes.

These two reagents can, therefore, be preserved at ambient temperature for several weeks.

At the time of use, the contents of reagent B were transferred to a flask containing reagent A. This flask was then placed in a water bath for incubation for 90 minutes at 30° C., thereby allowing formation of the desired colorants.

All documents cited herein are incorporated herein by reference.

We claim:

1. A process for preparing a composition containing a colorant on a colorant precursor, the process comprising the steps of:
   grinding at least one of a plant of the genus Medicago, a part of a plant of the genus Medicago, and a cell of a plant of the genus Medicago, said plant, part or cell being obtained from an in vitro culture, to produce a ground composition; and
   separating a fraction of said ground composition which is free of constituents having a molar mass greater than 3,500, said fraction containing said colorant precursor and being able to react in aqueous solution with 1,5 naphthoquinone so as to yield at least one colorant.

2. The process of claim 1, wherein said separating further comprises at least one of the following operations:
   filtering said ground composition and collecting a filtrate;
   decanting said ground composition and collecting a supernatant;
   centrifuging said ground composition and collecting a supernatant;
   extracting said ground composition with a solvent; and
   extracting said ground composition with a solvent, collecting an extract in said solvent and optionally evaporating said solvent from said extract.

3. The process according to claim 2, further comprising treating any of said filtrate, supernatant or extract to remove constituents having a molar mass of more than 1,500.

4. The process of claim 2 further comprising treating any of said filtrate, supernatant or extract to form a solid product.

5. The process of claim 1, wherein said in vitro culture is carried out in a medium containing lactose as a carbon source.

6. The process of claim 5, wherein said medium contains lactose as sole carbon source.

7. The process of claim 6, wherein said cell is a cell of a *Medicago sativa* plant.

8. The process of claim 6, wherein said cell is a cell of a plant selected from the group consisting of *Medicago sativa, Medicago falcata, Medicago intermedia, Medicago media, Medicago varia* and *Medicago versicolor*.

9. The process of claim 5 wherein said in vitro culture is carried out in the absence of light.

10. A composition containing at least one colorant precursor prepared according to the process of claim 1.

11. A composition containing at least one colorant precursor prepared according to the process of claim 6.

12. A composition containing at least one colorant precursor prepared according to the process of claim 7.

13. The composition of claim 10, said composition being in the form of a solution.

14. A composition containing at least one colorant precursor prepared according to the process of claim 4, wherein said solid is soluble in a solvent selected from the group consisting of water, a lower alkanol, methylene chloride and mixtures thereof.

15. The process of claim 1, wherein said separating results in a concentrating of said colorant precursor.

16. A composition prepared according to the process of claim 15.

17. The composition of claim 16 wherein said colorant precursor is present in said composition containing a colorant precursor in a concentration at least equal to that of an aqueous dispersion containing, per liter, 1 gram, dry weight, of a ground composition obtained from said in vitro culture when said culture is performed in a medium containing lactose as the only carbon source.

18. The composition according to claim 10 wherein said plant is selected from the group consisting of *Medicago sativa, Medicago falcata, Medicago intermedia, Medicago media, Medicago varia,* and *Medicago versicolor*.

19. The composition of claim 10, wherein said precursor is one which, after reaction with 1,4-naphthoquinone, yields at least one product selected from the group consisting of
   6,7,8,9-tetrahydro-dinaphtho[2,3-f:2',3'-h]-quinoline-5,10,11,16-tetraone;
   dinaphtho[2,3-c;2',3'-g]indoline-5,9, 14,15-tetraone;
   4b-hydroxy-4b,4c,10a, 10b,11,12,13-heptahydro-3-aza-anthra[1,4-def]naphtho[2',3'p]chrysene-5,10,14,19,20-pentaone; and
   dinaphtho[2,3-e;2',3'-g]indole-5,14,15-trione.

20. The process of claim 1 further comprising reacting said composition containing a colorant precursor with a quinone to produce a colorant and, optionally, isolating or purifying said colorant.

21. The process according to claim 20 wherein said quinone is selected from the group consisting of a 1,4-benzoquinone optionally substituted in at least one of positions 2 and 3, a 1,4-naphthoquinone optionally substituted in at least one of positions 5, 6, 7 and 8, and diphenoquinone.

22. The process of claim 21 wherein said quinone is an optionally substituted 1,4-benzoquinone corresponding to formula (I) or an optionally substituted 1,4-naphthoquinone corresponding to formula (II):

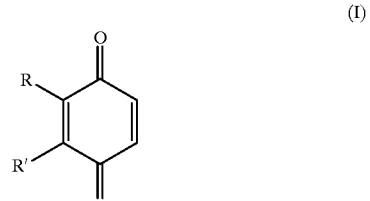

(I)

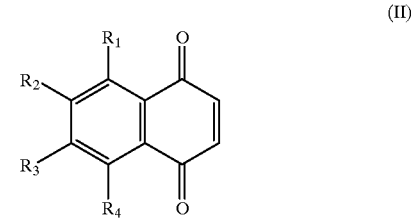

(II)

in which the substituents R, R', and $R_1$ to $R_4$ separately represent —H, hydroxy, $C_1$–$C_4$ alkyl, $C_1$–$C_4$ alkoxy, sulfonyl, or an optionally substituted heterocyclic or aryl group.

23. The process of claim 20 wherein said quinone is selected from the group consisting of 1,4-benzoquinone, 2-methyl-1,4-benzoquinone, 2-(4-methyl-2-furanyl)-1,4- benzoquinone, 2-hydroxy-1,4-benzoquinone, 2-phenyl-1,4-benzoquinone, 1,4-naphthoquinone, 5-hydroxy-1,4-naphthoquinone, 5-hydroxy-7-methyl-1,4-naphthoquinone, 6-methyl-1,4-naphthoquinone, and 5,8-dihydroxy-1,4-naphthoquinone.

24. The process of claim 20 wherein said reacting is carried out in a temperature range of about 20° C. to 100° C.

25. A colorant prepared according to the process of claim 20.

26. A colorant according to claim 25 selected from the group consisting of 6,7,8,9-tetrahydro-dinaphtho[2,3-f:2',3'-h] quinoline-5,10,11,16-tetraone,
 dinaphtho[2,3-c;2',3'-g]indoline-5,9,14,15-tetraone,
 4b-hydroxy-4b,4c,10a,10b,11,12,13-heptahydro-3-aza-anthra[1,4-def]naphtho[2',3-p]chrysene-5,10,14,19,20-pentaone, and
 dinaphtho[2,3-e;2',3'-g]indole-5,14,15-trione.

27. A colorant selected from the group consisting of 6,7,8,9-tetrahydro-dinaphtho[2,3-f:2',3'-h] quinoline-5,10,11,16-tetraone,
 dinaphtho[2,3-c;2',3'-g]indoline-5,9,14,15-tetraone,
 4b-hydroxy-4b,4c,10a,10b,11,12,13-heptahydro-3-aza-anthra[1,4-def]naphtho[2',3-p]chrysene-5,10,14,19,20-pentaone, and
 dinaphtho[2,3-e;2',3'-g]indole-5,14,15-trione.

28. A kit for the preparation of a dyeing composition, said kit comprising, in separate containers whose contents are mixed at the time of use, at least one colorant precursor and at least one quinone, said precursor possessing the following characteristics:

it is a product existing naturally in a cell of a plant belong to the genus Medicago, and
 it can react with said quinone so as to yield at least one colorant.

29. A dyeing composition comprising the colorant of claim 25.

30. A dyeing composition comprising the colorant of claim 26.

31. A dyeing composition comprising the colorant of claim 27.

32. The kit of claim 28 wherein said plant is selected from the group consisting of *Medicago sativa, Medicago falcata, Medicago intermedia, Medicago media, Medicago varia,* and *Medicago versicolor.*

33. A kit according to claim 32 wherein said quinone is selected from the group consisting of 1,4-benzoquinones, 1,4-naphthoquinones and diphenoquinones.

\* \* \* \* \*